United States Patent
Nerenberg

(10) Patent No.: US 7,041,286 B2
(45) Date of Patent: May 9, 2006

(54) COMPOSITION FOR MITIGATING A PERNICIOUS THROMBOTIC EVENT

(76) Inventor: Arnold P. Nerenberg, 7238 S. Painter Ave., Whittier, CA (US) 90602

(*) Notice: Subject to any disclaimer, the term of this patent is extended or adjusted under 35 U.S.C. 154(b) by 13 days.

(21) Appl. No.: 10/625,305

(22) Filed: Jul. 23, 2003

(65) Prior Publication Data

US 2005/0019319 A1    Jan. 27, 2005

(51) Int. Cl.
  *A61K 31/44*   (2006.01)
  *A61K 38/43*   (2006.01)
  *A01N 43/40*   (2006.01)
  *A01N 59/06*   (2006.01)
  *C06B 25/10*   (2006.01)

(52) U.S. Cl. ............ 424/94.1; 149/101; 424/682; 514/356

(58) Field of Classification Search ........ 435/41; 424/439
  See application file for complete search history.

(56) References Cited

U.S. PATENT DOCUMENTS

| | | |
|---|---|---|
| 4,654,209 A | 3/1987 | Leslie et al. |
| 5,006,516 A | 4/1991 | Helbig et al. |
| 5,776,498 A | 7/1998 | McCarty |
| 5,948,443 A | 9/1999 | Riley et al. |
| 5,962,413 A | 10/1999 | Garfield et al. |
| 6,015,577 A | 1/2000 | Eisert et al. |
| 6,048,846 A * | 4/2000 | Cochran ............ 514/168 |
| 6,203,819 B1 | 3/2001 | Fine |
| 6,245,811 B1 | 6/2001 | Horrobin et al. |
| 6,261,250 B1 | 7/2001 | Phillips |
| 6,369,073 B1 | 4/2002 | Giannessi et al. |
| 6,391,895 B1 | 5/2002 | Towart et al. |
| 6,432,986 B1 | 8/2002 | Levin |
| 6,669,971 B1 * | 12/2003 | Kato et al. ............ 426/46 |
| 2002/0025917 A1 | 2/2002 | Pappalardo |
| 2002/0034546 A1 | 3/2002 | Ullah et al. |
| 2002/0034555 A1 | 3/2002 | Gelber et al. |
| 2002/0052348 A1 | 5/2002 | Giannessi et al. |

* cited by examiner

*Primary Examiner*—Michael Wityshyn
*Assistant Examiner*—Deborah K. Ware
(74) *Attorney, Agent, or Firm*—Schmeiser, Olsen & Watts

(57) ABSTRACT

A composition. The composition comprises aspirin, magnesium, and nattokinase, and either niacin or nitroglycerine. The composition has a structural form of: a chewable form, a dissolvable form, a liquid form, a spray form, or a suppository form. The structural form is suitable for being introduced into the body of a person, such as by means of a body cavity of the person. The composition may be used for mitigating adverse effects of an imminent or actually-occurring pernicious thrombotic event, such as a heart attack or stroke, in the person.

31 Claims, 1 Drawing Sheet

COMPOSITION FOR MITIGATING A PERNICIOUS THROMBOTIC EVENT

BACKGROUND OF THE INVENTION

1. Technical Field

The present invention relates to a composition for mitigating adverse effects of an imminent or actually-occurring pernicious thrombotic event, such as a heart attack or stroke, in a person.

2. Related Art

An individual having a heart attack or experiencing symptoms indicating that a heart attack is imminent or probable needs to have medical intervention by medical professionals as soon as possible. Accordingly, there is a need to mitigate the damage that could potentially be done to the individual's coronary system prior to said medical intervention.

SUMMARY OF THE INVENTION

The present invention provides a composition, comprising: aspirin, magnesium, and nattokinase, and either niacin or nitroglycerine, said composition having a structural form that is suitable for being introduced into a body of a person.

The present invention advantageously provides a composition for mitigating adverse effects of an imminent or actually-occurring pernicious thrombotic event, such as a heart attack or stroke, in a person.

DETAILED DESCRIPTION OF THE INVENTION

If a person experiences symptoms of an imminent or actually-occurring heart attack, the person needs medical intervention by medical professionals as soon as possible. Accordingly, the present invention provides a therapeutic composition suitable for being introduced into the body (e.g., by means of a body cavity) of a person. This composition is adapted to provide therapeutic benefits to the person during the critical period prior to the arrival or availability of said medical intervention. The therapeutic benefits mitigate the damage that could potentially be done to the individual's coronary system prior to said medical intervention The composition of the present invention includes aspirin, magnesium, and nattokinase, and niacin or nitroglycerine. The composition may include one or more additional ingredients as will be discussed infra. The composition is adapted to be introduced into the body (e.g., body cavity) of the person for mitigating adverse effects of an imminent or actually-occurring heart attack or stroke in the person. Thus, the composition has a structural form being suitable for introduction of the composition into the body a person such as, inter alia, one of the structural forms of FIGS. 1–4 or related structural forms as described infra, which depict structural forms of the composition of the present invention in accordance with embodiments thereof.

Figure 1:
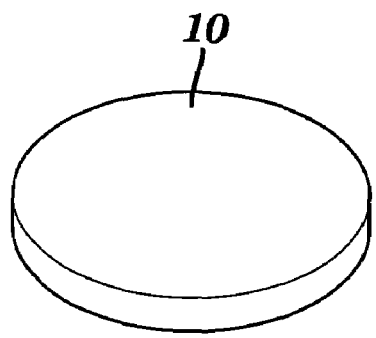
FIGS. 1–4 depict structural forms of a composition, in accordance with embodiments of the present invention.

FIG. 1 depicts chewable form 10, such as a wafer or a chewable pill. Although FIG. 1 shows the chewable form 10 as being round, the chewable form may have any geometric shape, (e.g., circular, elliptical, rectangular square, triangular, etc.). The size of the chewable form 10 is of a size sufficient to contain all ingredients of the composition in the amounts desired. For example, the chewable form 10 may be, inter alia, circular with a diameter of 1½ inches and a thickness of ½ inch. The chewable form 10 is adapted to be chewed by the person for quick ingestion in the event an imminent or actually-occurring heart attack in a person.

The structural form of the present invention may comprise a dissolvable form such as a dissolvable wafer or dissolvable pill, which may be constituted structurally similar to the chewable form 10 shown in FIG. 1. The dissolvable form may dissolve in the mouth of the person when held under the person's tongue, for quick absorption into the bloodstream of the person in the event an imminent or actually-occurring heart attack in the person.

Figure 2:
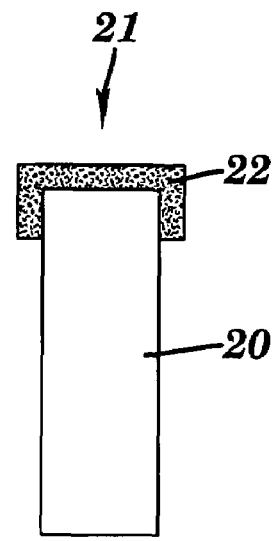

FIG. 2 depicts the liquid form 20 contained in a vial or equivalent container 21 having a top 22. The top 22 may be, inter alia, a screwable top, a puncturable top, etc. The liquid form 20 is adapted to be swallowed by the person for quick ingestion in the event an imminent or actually-occurring heart attack in a person. The liquid form 20 may alternatively be adapted to be introduced into the body of the person by injection through use of a needle or syringe (at any suitable point of injection on the person's body).

The structural form of the present invention may comprise an alternative dissolvable form such as a liquid, which may be constituted structurally similar to the liquid form 20 form shown in FIG. 1. The dissolvable form may dissolve in the mouth of the person when held under the person's tongue, for quick absorption into the bloodstream of the person in the event an imminent or actually-occurring heart attack in the person.

Figure 3:
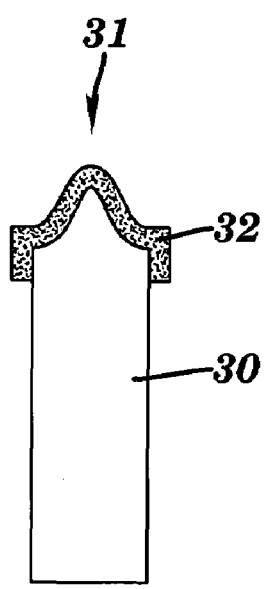

FIG. 3 depicts the spray form 30 contained in a spray bottle or equivalent container 31 having a cover 32. The cover 32 may be, inter alia, a screwable cover. The spray form 30 may be any type of spray (e.g., aerosol spray in a pressurized container 31) as is known in the art. The spray form 30 is adapted to be sprayed into the nasal cavity of the person for quick absorption into the bloodstream of the person in the event an imminent or actually-occurring heart attack in the person.

Figure 4:
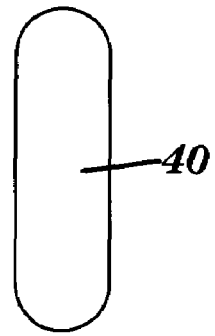

FIG. 4 depicts a suppository form 40 for insertion into the anal cavity of the person for quick absorption into the bloodstream of the person in the event an imminent or actually-occurring heart attack in the person.

Irrespective of the structural form of the composition, the ingredients of the composition may be distributed homogeneously or inhomogeneously within the composition.

The composition of the present invention comprises four basic ingredients for providing a four-weapon simultaneous assault on the imminent or actually-occurring heart attack experienced by the person, inasmuch as the composition provides a blood thinner (aspirin), a blood clot buster (nattokinase), a means for preventing or reducing damage to the heart (magnesium), and a blood vessel dilator (niacin or nitroglycerine). Thus, the different therapeutic roles played by each of the four basic ingredients composition is analogous to a military force simultaneously attacking the enemy in all four directions: north, south, east, and west. As another military analogy, the different therapeutic roles played by each of the four basic ingredients composition is analogous to using the four different branches of the armed services (i.e., army, navy, air force, marines) to attack the enemy.

As a blood thinner, aspirin helps to prevent the formation of blood clots. As a clot buster, nattokinase attacks fibrin clumps that clot blood vessels. Nattokinase is an enzyme produced by a fermentation process in which the bacteria bacillus natto is added to boiled soybeans. If the person has a deficiency of magnesium, the person is likely to suffer more heart damage during a heart attack than does one not having a magnesium deficiency. As a blood vessel dilator, niacin or nitroglycerine improve blood circulation, thereby improving the transport of oxygen to the heart.

The composition of the present invention may additionally comprise one or more of the following ingredients: L-carnitine, alpha lipoic acid, L-arginine, and coenzyme Q10. L-carnitine (e.g., proprionyl L-carnitine) helps to increase blood flow to the heart and to reduce or prevent heart enlargement. Alpha lipoic acid is a fat and water soluble antioxidant that protects tissues from damage associated with low oxygen supply during a heart attack. L-arginine increases local production of nitric oxide, which dilates the smooth muscle found in the linings of blood vessels, thereby leading to a lowering of blood pressure. L-arginine also inhibits aggregation of platelets wherein said platelets promote blood clotting. Coenzyme Q10 increases blood circulation and enhances oxygen levels in the heart muscle.

The ingredients comprised by the composition of the present invention may each have a therapeutically effective amount for mitigating adverse effects of an imminent or actually-occurring heart attack in the person. The therapeutically effective amount may be different for different persons. Accordingly, the ingredients comprised by the composition of the present invention may exist, inter alia, in the amount shown in Table 1.

TABLE 1

| Ingredient | Amount |
| --- | --- |
| Aspirin | 650 to 975 mg |
| Magnesium | 5000 to 15000 mg |
| Nattokinase | 150 to 3000 mg |
| Niacin | 500 to 3000 mg |
| Nitroglycerine | 0.4 to 2.5 mg |
| L-carnitine | 2000 to 9000 mg |
| Alpha lipoic acid | 200 to 10000 mg |
| L-arginine | 2000 to 12000 mg |
| Coenzyme Q10 | 300 to 6000 mg |

The ingredients of the composition may be packaged with any base ingredient (e.g., soybean oil, lecithin, etc.) known to a person of ordinary skill in the art as being useful and practical for packaging analogous compositions.

While the preceding discussion focused on a composition that mitigates adverse effects of an imminent or actually-occurring heart attack in a person, the composition of the present invention may be modified by adding Vitamin C, zinc, and Vitamin E in therapeutic amounts so as to mitigate adverse effects resulting from heart surgery following a heart attack or otherwise conducted in the absence of a heart attack. The Vitamin C, zinc, and Vitamin E may exist in the composition in the following amounts: Vitamin C (1000 to 10000 mg); zinc (90 to 300 mg); and Vitamin E (2000 to 10000 International Units).

It is noted that while a heart attack may be accompanied by blood clotting in a coronary artery so as to impede or block blood flow to the heart, a stroke may analogously be accompanied by blood clotting in a blood vessel leading to the brain so as to impede or block blood flow to the brain. Therefore, while the preceding discussion related to the beneficial effect of the ingredients of the composition of the present invention for mitigating adverse effects of an imminent or actually-occurring heart attack in a person, the composition of the present invention is similarly useful for mitigating adverse effects of an imminent or actually-occurring stroke in the person. More generally, the composition of the present invention is useful for mitigating adverse effects of an imminent or actually-occurring pernicious thrombotic event in the person. Examples of pernicious thrombotic event include heart attack, stroke, etc.

While the preceding discussion focused on a composition that mitigates adverse effects of an imminent or actually-occurring thrombotic event in a person, the composition of the present invention may also be used to prevent a thrombotic event that has a heightened probability of occurring in the person due to the person anticipating being subjected to a high level of physical or emotional stress; e.g., lifting weights in preparation for (or during) a weight-lifting contest, engaging in battle during a military encounter, being a victim during an airplane hijacking, etc.

While embodiments of the present invention have been described herein for purposes of illustration, many modifications and changes will become apparent to those skilled in the art. Accordingly, the appended claims are intended to encompass all such modifications and changes as fall within the true spirit and scope of this invention.

What is claimed is:

1. A composition, comprising: aspirin, magnesium, and nattokinase, and either niacin or nitroglycerine, said composition having a structural form that is suitable for being introduced into a body of a person.

2. The composition of claim 1, wherein the composition is adapted to be introduced into the body of the person for mitigating adverse effects of an imminent or actually-occurring pernicious thrombotic event in the person.

3. The composition of claim 2, wherein the pernicious thrombotic event in the person is a heart attack or stroke in the person.

4. The composition of claim 1, wherein the aspirin, magnesium, nattokinase, and niacin or nitroglycerine each have a therapeutically effective amount for mitigating adverse effects of an imminent or actually-occurring pernicious thrombotic event in the person.

5. The composition of claim 4, wherein the pernicious thrombotic event in the person is a heart attack or stroke in the person.

6. The composition of claim 1, wherein the structural form is a chewable form, and wherein the chewable form is adapted to being introduced into the mouth of the person.

7. The composition of claim 6, wherein the chewable form comprises a wafer or a chewable tablet.

8. The composition of claim 6, wherein the structural form is a dissolvable form, and wherein the dissolvable form is adapted to being introduced into the mouth of the person.

9. The composition of claim 1, wherein the structural form is a liquid form.

10. The composition of claim 1, wherein the structural form is a spray form, and wherein the spray form is adapted to being introduced into the nasal cavity of the person.

11. The composition of claim 1, wherein the structural form is a suppository form, and wherein the suppository form is adapted to being introduced into the anal cavity of the person.

12. The composition of claim 1, wherein the composition comprises niacin.

13. The composition of claim 12, wherein the aspirin has an amount in a range of 650 to 975 mg, wherein the magnesium has an amount in a range of 300 to 3000 mg, wherein the nattokinase has an amount in a range of 150 to 3000 mg, and wherein the niacin has an amount in a range of 500 to 3000 mg.

14. The composition of claim 12, further comprising L-carnitine.

15. The composition of claim 14, wherein the aspirin has an amount in a range of 650 to 975 mg, wherein the magnesium has an amount in a range of 300 to 3000 mg, wherein the nattokinase has an amount in a range of 150 to 3000 mg, wherein the niacin has an amount in a range of 500 to 3000 mg, and wherein the L-carnitine has an amount in a range of 2000 to 9000 mg.

16. The composition of claim 14, further comprising alpha lipoic acid.

17. The composition of claim 16, wherein the aspirin has an amount in a range of 650 to 975 mg, wherein the magnesium has an amount in a range of 300 to 3000 mg, wherein the nattokinase has an amount in a range of 150 to 3000 mg, wherein the niacin has an amount in a range of 500 to 3000 mg, wherein the L-carnitine has an amount in a range of 2000 to 9000 mg, and wherein the alpha lipoic acid has an amount in a range of 200 to 10000 mg.

18. The composition of claim 16, further comprising L-arginine.

19. The composition of claim 18, wherein the aspirin has an amount in a range of 650 to 975 mg, wherein the magnesium has an amount in a range of 300 to 3000 mg, wherein the nattokinase has an amount in a range of 150 to 3000 mg, wherein the niacin has an amount in a range of 500 to 3000 mg, wherein the L-carnitine has an amount in a range of 2000 to 9000 mg, wherein the alpha lipoic acid has an amount in a range of 200 to 10000 mg, and wherein the L-arginine has an amount in a range of 2000 to 12000 mg.

20. The composition of claim 18, further comprising coenzyme Q10.

21. The composition of claim 20, wherein the aspirin has an amount in a range of 650 to 975 mg, wherein the magnesium has an amount in a range of 300 to 3000 mg, wherein the nattokinase has an amount in a range of 150 to 3000 mg, wherein the niacin has an amount in a range or 500 to 3000 mg, wherein the L-carnitine has an amount in a range of 2000 to 9000 mg, wherein the alpha lipoic acid has an amount in a range of 200 to 10000 mg, wherein the L-arginine has an amount in a range of 2000 to 12000 mg, and wherein the coenzyme Q10 has an amount in a range of 300 to 6000 mg.

22. The composition of claim 1, wherein the composition comprises nitroglycerine.

23. The composition of claim 22, wherein the aspirin has an amount in a range of 650 to 975 mg, wherein the magnesium has an amount in a range of 300 to 3000 mg, wherein the nattokinase has an amount in a range of 150 to 3000 mg, and wherein the nitroglycerine has an amount in a range of 0.4 to 2.5 mg.

24. The composition of claim 22, further comprising L-carnitine.

25. The composition of claim 24, wherein the aspirin has an amount in a range of 650 to 975 mg, wherein the magnesium has an amount in a range of 300 to 3000 mg, wherein the nattokinase has an amount in a range of 150 to 3000 mg, wherein the nitroglycerine has an amount in a range of 0.4 to 2.5 mg, and wherein the L-carnitine has an amount in a range of 2000 to 9000 mg.

26. The composition of claim 24, further comprising alpha lipoic acid.

27. The composition of claim 26, wherein the aspirin has an amount in a range of 650 to 975 mg, wherein the magnesium has an amount in a range of 300 to 3000 mg, wherein the nattokinase has an amount in a range of 150 to 3000 mg, wherein the nitroglycerine has an amount in a range of 0.4 to 2.5 mg, wherein the L-carnitine has an amount in a range of 2000 to 9000 mg, and wherein the alpha lipoic acid has an amount in a range of 200 to 10000 mg.

28. The composition of claim 26, farther comprising L-arginine.

29. The composition of claim 28, wherein the aspirin has an amount in a range of 650 to 975 mg, wherein the magnesium has an amount in a range of 300 to 3000 mg, wherein the nattokinase has an amount in a range of 150 to 3000 mg, wherein the nitroglycerine has an amount in a range of 0.4 to 2.5 mg, wherein the L-carnitine has an amount in a range of 2000 to 9000 mg, wherein the alpha lipoic acid has an amount in a range of 200 to 10000 mg, and wherein the L-arginine has an amount in a range of 2000 to 12000 mg.

30. The composition of claim 28, further comprising coenzyme Q10.

31. The composition of claim 30, wherein the aspirin has an amount in a range of 650 to 975 mg, wherein the magnesium has an amount in a range of 300 to 3000 mg, wherein the nattokinase has an amount in a range of 150 to 3000 mg, wherein the nitroglycerine has an amount in a range of 0.4 to 2.5 mg, wherein the L-carnitine has an amount in a range of 2000 to 9000 mg, wherein the alpha lipoic acid has an amount in a range of 200 to 10000 mg, and wherein the L-arginine has an amount in a range of 2000 to 12000 mg, and wherein the coenzyme Q10 has an amount in a range of 300 to 6000 mg.

* * * * *

UNITED STATES PATENT AND TRADEMARK OFFICE
CERTIFICATE OF CORRECTION

| | |
|---|---|
| PATENT NO. | : 7,041,286 B2 |
| APPLICATION NO. | : 10/625305 |
| DATED | : May 9, 2006 |
| INVENTOR(S) | : Nerenberg |

It is certified that error appears in the above-identified patent and that said Letters Patent is hereby corrected as shown below:

On the Title Page
Under (76) Inventor, delete "7238 S. Painter Ave.,"

Column 6
Line 23, delete "farther" and insert -- further --

Signed and Sealed this

Twenty-second Day of August, 2006

JON W. DUDAS
*Director of the United States Patent and Trademark Office*